United States Patent
Buettelmann et al.

(10) Patent No.: US 7,378,435 B2
(45) Date of Patent: May 27, 2008

(54) ARYL-ISOXAZOLE-4-CARBONYL-INDOLE-CARBOXYLIC ACID AMIDE DERIVATIVES

(75) Inventors: Bernd Buettelmann, Schopfheim (DE); Bo Han, Shanghai (CN); Henner Knust, Rheinfelden (DE); Matthias Nettekoven, Grenzach-Wyhlen (DE); Andrew Thomas, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 52 days.

(21) Appl. No.: 11/543,178

(22) Filed: Oct. 4, 2006

(65) Prior Publication Data

US 2007/0082936 A1    Apr. 12, 2007

(30) Foreign Application Priority Data

Oct. 11, 2005   (EP)   .................. 05109424

(51) Int. Cl.
  *A61K 31/42*   (2006.01)
  *C07D 413/02*   (2006.01)
(52) U.S. Cl. ...................... 514/378; 548/248
(58) Field of Classification Search ............... 514/378; 548/248
  See application file for complete search history.

(56) References Cited

FOREIGN PATENT DOCUMENTS

| WO | WO 01/29015 | 4/2001 |
|---|---|---|
| WO | WO 02/50062 A2 | 6/2002 |
| WO | WO 02/814784 A1 | 10/2002 |
| WO | WO 03/004027 | 1/2003 |
| WO | WO 2005/123672 A2 | 12/2005 |

OTHER PUBLICATIONS

McNamara et al., Psychobiology (1993), vol. 21(2) pp. 101-108.
Hamper et al., J. Agric. Food Chem. (1995), vol. 43, pp. 219-228.

*Primary Examiner*—Kamal A. Saeed
(74) *Attorney, Agent, or Firm*—George W. Johnston; Patricia S. Rocha-Tramaloni; Kimberly J. Prior

(57) ABSTRACT

The present invention is concerned with aryl-isoxazole-4-carbonyl-indole-carboxylic acid amide derivatives of formula I

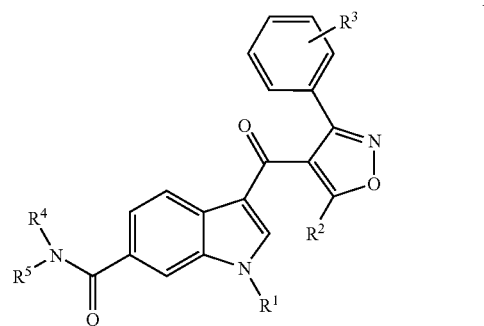

wherein
  $R^1$, $R^2$, $R^3$, $R^4$, and $R^5$ are as defined in the specification and claims and with their pharmaceutically acceptable acid addition salts. The invention also relates to methods for preparing such compounds. This class of compounds has a high affinity and selectivity for GABA A α5 receptor binding sites and might be useful as cognitive enhancer or for the treatment of cognitive disorders like Alzheimer's disease. Thus, the invention also is concerned with pharmaceutical compositions containing compounds of formula I or their pharmaceutically acceptable acid addition salts and methods for the treatment of GABA Aα5 mediated diseases, including Alzheimer's disease.

33 Claims, No Drawings

ARYL-ISOXAZOLE-4-CARBONYL-INDOLE-CARBOXYLIC ACID AMIDE DERIVATIVES

PRIORITY TO RELATED APPLICATIONS

This application claims the benefit of European Application No. 05109424.1, filed Oct. 11, 2005, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits.

Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in *Psychobiology*, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or β3 receptor binding sites can be used to provide a medicament which is useful for enhancing cognition with reduced or without proconvulsant activity. It is also possible to use GABA A α5 inverse agonists which are not free of activity at GABA A α1 and/or α2 and/or α3 receptor binding sites but which are functionally selective for α5 containing subunits. However, inverse agonists which are selective for GABA A α5 subunits and are relatively free of activity at GABA A α1, α2 and α3 receptor binding sites are preferred.

SUMMARY OF THE INVENTION

The present invention provides aryl-isoxazole-4-carbonyl-indole-carboxylic acid amide derivatives of formula I

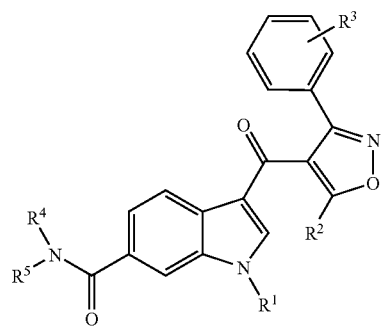

wherein
$R^1$ is hydrogen, lower alkyl or aryl;
$R^2$ is lower alkyl;
$R^3$ is hydrogen or halogen;
$R^4$ and $R^5$ are each independently hydrogen, lower alkyl, lower alkinyl, —$(CH_2)_n$-cycloalkyl, —$(CH_2)_n$-heteroaryl, —$(CH_2)_n$-heterocyclyl or —$(CH_2)_n$—OH;
n is 0, 1, 2 or 3;

and their pharmaceutically acceptable acid addition salts.

The present invention also provides pharmaceutical compositions that comprise a compound of the invention and a pharmaceutically acceptable carrier. The invention further provides processes for the preparation of compounds and compositions of the invention.

This class of compounds have a high affinity and selectivity for GABA A α5 receptor binding sites and might be useful as cognitive enhancers for the treatment of cognitive disorders. The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon residue containing from 1-7, preferably from 1-4, carbon atoms, for example, methyl, ethyl, propyl, isopropyl, n-butyl, i-butyl, t-butyl and the like.

The term "lower alkinyl" denotes a straight- or branched-chain carbon group containing from 2-7, preferably from 2-4, carbon atoms, containing at least one triple bond.

The term "aryl" denotes an aromatic carbon ring, for example a phenyl, benzyl or naphthyl group. A preferred aryl group is phenyl.

The term "halogen" denotes chlorine, iodine, fluorine and bromine.

The term "cycloalkyl" denotes a cyclic alkyl ring, having from 3 to 7 carbon ring atoms, for example, cyclopropyl, cyclopentyl or cyclohexyl.

The term "heterocyclyl" denotes a cyclic saturated ring, having from one to three heteroatoms, selected from N, O and S, with the remaining ring atoms being carbon atoms, for example the following rings: morpholin, thiomorpholin, piperazin, tetrahydropyran, piperidin, pyrrolidin and tetrahydrofuran.

The term "heteroaryl" denotes an aromatic 5 or 6 membered ring containing from one to three heteroatoms, selected from N, O and S atoms, with the remaining ring atoms being carbon atoms. Examples of such aromatic heteroaryl rings are isoxazole, furan, pyridine, thiophen, imidazol, oxazol and pyrazin.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention provides aryl-isoxazole-4-carbonyl-indole-carboxylic acid amide derivatives of formula I

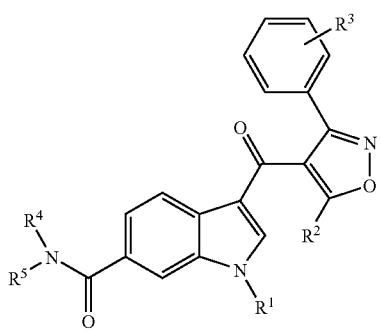

wherein
$R^1$ is hydrogen, lower alkyl or aryl;
$R^2$ is lower alkyl;
$R^3$ is hydrogen or halogen;
$R^4$ and $R^5$ are each independently hydrogen, lower alkyl, lower alkinyl, —$(CH_2)_n$-cycloalkyl, —$(CH_2)_n$-heteroaryl, —$(CH_2)_n$-heterocyclyl or —$(CH_2)_n$—OH;
n is 0, 1, 2 or 3;

and their pharmaceutically acceptable acid addition salts.

Preferred compounds are those which have a binding activity (hKi) of lower than 0.01 μM, are selective for GABA A α5 subunits, and are relatively free of activity at GABA A α1, α2 and α3 receptor binding sites.

Preferred compounds of formula I are those, in which $R^1$, $R^2$ and $R^3$ are as described above, $R^4$ is hydrogen and $R^5$ is lower alkinyl, for example the following compounds
3-(5-methyl-3-phenyl-isoxazole-4-carbonyl)-1H-indole-6-carboxylic acid prop-2-ynylamide,
3-[3-(4-fluoro-phenyl)-5-methyl-isoxazole-4-carbonyl]-1H-indole-6-carboxylic acid prop-2-ynylamide and
3-[3-(3-fluoro-phenyl)-5-methyl-isoxazole-4-carbonyl]-1-phenyl-1H-indole-6-carboxylic acid prop-2-ynylamide.

Furthermore, preferred are compounds, wherein $R^1$, $R^2$ and $R^3$ are as described above, $R^4$ is hydrogen and $R^5$ is $(CH_2)_n$-cycloalkyl, for example the following compounds
3-[3-(4-fluoro-phenyl)-5-methyl-isoxazole-4-carbonyl]-1H-indole-6-carboxylic acid cyclopropylmethyl-amide,
3-(5-methyl-3-phenyl-isoxazole-4-carbonyl)-1H-indole-6-carboxylic acid cyclopropylmethyl-amide,
3-(5-methyl-3-phenyl-isoxazole-4-carbonyl)-1H-indole-6-carboxylic acid cyclopropylamide,
3-(5-methyl-3-phenyl-isoxazole-4-carbonyl)-1H-indole-6-carboxylic acid cyclobutylamide,
3-[3-(4-fluoro-phenyl)-5-methyl-isoxazole-4-carbonyl]-1H-indole-6-carboxylic acid cyclopentylamide,
3-[3-(4-fluoro-phenyl)-5-methyl-isoxazole-4-carbonyl]-1H-indole-6-carboxylic acid cyclopropylamide and
3-[3-(4-fluoro-phenyl)-5-methyl-isoxazole-4-carbonyl]-1H-indole-6-carboxylic acid cyclobutylamide.

Preferred compounds are further those, in which $R^1$, $R^2$ and $R^3$ are as described above, $R^4$ is hydrogen and $R^5$ is $(CH_2)_n$-heteroaryl, for example the following compounds
3-(5-Methyl-3-phenyl-isoxazole-4-carbonyl)-1H-indole-6-carboxylic acid [2-(1H-imidazol-4-yl)-ethyl]-amide,
3-(5-methyl-3-phenyl-isoxazole-4-carbonyl)-1H-indole-6-carboxylic acid (pyridin-2-ylmethyl)-amide,
3-(5-methyl-3-phenyl-isoxazole-4-carbonyl)-1H-indole-6-carboxylic acid (furan-2-ylmethyl)-amide,
3-[3-(4-fluoro-phenyl)-5-methyl-isoxazole-4-carbonyl]-1H-indole-6-carboxylic acid [2-(1H-imidazol-4-yl)-ethyl]-amide,
3-[3-(4-fluoro-phenyl)-5-methyl-isoxazole-4-carbonyl]-1H-indole-6-carboxylic acid (pyridin-2-ylmethyl)-amide,
3-[3-(4-fluoro-phenyl)-5-methyl-isoxazole-4-carbonyl]-1H-indole-6-carboxylic acid (furan-2-ylmethyl)-amide,
3-[3-(4-fluoro-phenyl)-5-methyl-isoxazole-4-carbonyl]-1H-indole-6-carboxylic acid (pyridin-4-ylmethyl)-amide and
3-[3-(4-fluoro-phenyl)-5-methyl-isoxazole-4-carbonyl]-1H-indole-6-carboxylic acid (pyridin-3-ylmethyl)-amide.

Furthermore, preferred are compounds, wherein $R^1$, $R^2$ and $R^3$ are as described above, $R^4$ is hydrogen and $R^5$ is $(CH_2)_n$-heterocyclyl, for example the following compounds
3-(5-methyl-3-phenyl-isoxazole-4-carbonyl)-1H-indole-6-carboxylic acid (2-morpholin-4-yl-ethyl)-amide,
3-(5-methyl-3-phenyl-isoxazole-4-carbonyl)-1H-indole-6-carboxylic acid (tetrahydro-pyran-4-yl)-amide,
3-[3-(4-fluoro-phenyl)-5-methyl-isoxazole-4-carbonyl]-1H-indole-6-carboxylic acid (2-morpholin-4-yl-ethyl)-amide,
3-[3-(4-fluoro-phenyl)-5-methyl-isoxazole-4-carbonyl]-1H-indole-6-carboxylic acid (3-morpholin-4-yl-propyl)-amide,
3-[3-(4-fluoro-phenyl)-5-methyl-isoxazole-4-carbonyl]-1H-indole-6-carboxylic acid (tetrahydro-pyran-4-yl)-amide and
3-[3-(3-fluoro-phenyl)-5-methyl-isoxazole-4-carbonyl]-1-phenyl-1H-indole-6-carboxylic acid (tetrahydro-pyran-4-yl) -amide.

Preferred compounds are further those, in which $R^1$, $R^2$ and $R^3$ are as described above, $R^4$ is hydrogen and $R^5$ is $(CH_2)_n$—OH, for example the following compound
3-[3-(4-fluoro-phenyl)-5-methyl-isoxazole-4-carbonyl]-1H-indole-6-carboxylic acid (2-hydroxy-ethyl)-amide.

The present compounds of formula I and their pharmaceutically acceptable salts can be prepared by methods known in the art, for example, by processes described below, which process comprises reacting a compound of formula

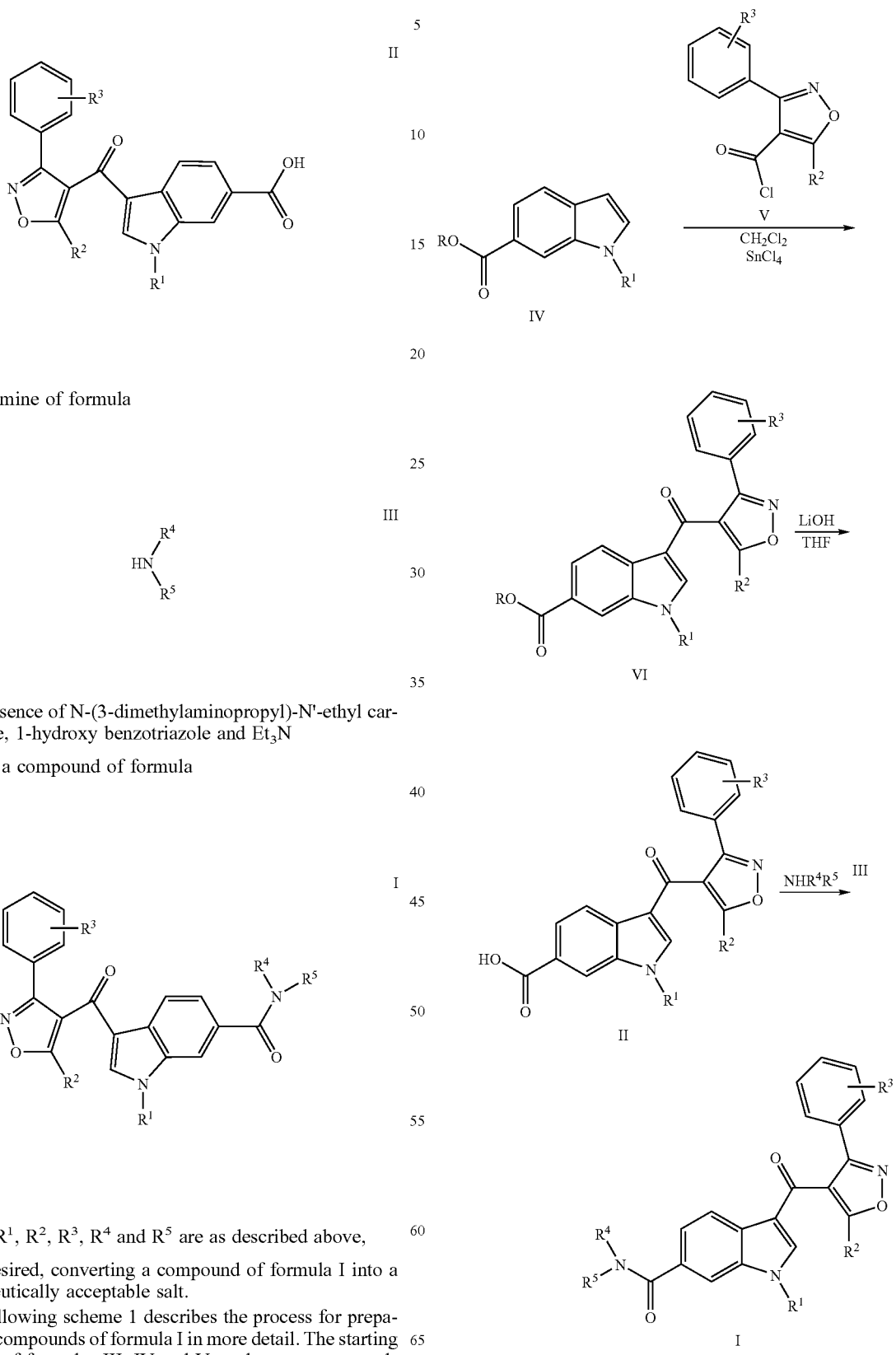

with an amine of formula

III in the presence of N-(3-dimethylaminopropyl)-N'-ethyl carbodiimide, 1-hydroxy benzotriazole and Et₃N to obtain a compound of formula

I wherein R¹, R², R³, R⁴ and R⁵ are as described above, and, if desired, converting a compound of formula I into a pharmaceutically acceptable salt.

The following scheme 1 describes the process for preparation of compounds of formula I in more detail. The starting materials of formulas III, IV and V are known compounds or can be prepared according to methods known in the art.

$R^1$, $R^2$, $R^3$, $R^4$ and $R^5$ are as described above and R is lower alkyl.

According to scheme 1, compounds of formula I can be prepared as follows: To a stirred solution of an indole-6-carboxylate (commercially available) of formula IV in dry $CH_2Cl_2$ under argon at 0° C. is added $SnCl_4$ in one portion. The mixture is stirred for about 40 min at room temperature and then a corresponding compound of formula V (Prepared from the corresponding acid according to: *J. Agric. Food Chem.* 1995, 43, 219-228.) is added at 0 °C. followed by the addition of nitromethane in one portion. The mixture is stirred for about 15 minutes at 0° C.

To the solution of the obtained carboxylic acid methyl ester of formula VI in THF and $H_2O$, is added $LiOH.H_2O$ in one portion. The reaction mixture is heated under reflux for about 16 h to obtain the corresponding carboxylic acid of formula II. A solution of a compound of formula II, N-(3-dimethylaminopropyl)-N'-ethyl carbodiimide, 1-hydroxy benzotriazole, $Et_3N$ and an amine of formula III in DMF is reacted at room temperature overnight to obtain a compound of formula I.

As mentioned earlier, the compounds of formula I and their pharmaceutically usable salts possess valuable pharmacological properties. The compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2β3γ2, α3β3γ2 and α5β3γ2.

Cell pellets were suspended in Krebs-tris buffer (4.8 mM KCl, 1.2 mM CaCl2, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of $10-10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and all were found to possess a Ki value for displacement of [3H]flumazenil from a 5 subunits of the rat GABA A receptor of 100 nM or less. In a preferred embodiment the compounds of the invention are binding selective for the α5 subunit relative to the α1, α2 and α3 subunit.

| Example No. | Ki[μM] hα5 |
| --- | --- |
| 1 | 0.00645 |
| 2 | 0.00545 |
| 3 | 0.0029 |
| 4 | 0.00265 |
| 5 | 0.00395 |
| 6 | 0.0033 |
| 7 | 0.0053 |
| 8 | 0.003 |
| 9 | 0.00435 |
| 11 | 0.00545 |
| 12 | 0.0026 |
| 13 | 0.00565 |
| 14 | 0.00455 |
| 15 | 0.00484 |
| 16 | 0.00365 |
| 17 | 0.0043 |
| 18 | 0.00185 |
| 20 | 0.00325 |
| 21 | 0.005 |
| 22 | 0.00975 |
| 23 | 0.00305 |
| 24 | 0.00225 |
| 25 | 0.00675 |
| 49 | 0.0085 |
| 50 | 0.0098 |

The present invention also provides pharmaceutical compositions containing compounds of formula I and/or their pharmaceutically acceptable acid addition salts. Such compositions can be in the form of tablets, coated tablets, dragees, hard and soft gelatin capsules, solutions, emulsions or suspensions. The pharmaceutical compositions also can be in the form of suppositories or injectable solutions.

The pharmaceutical compositions of the invention contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragees and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragees, hard and soft gelatin capsules, solutions, emulsions, or suspensions. The pharmaceutical compositions also can be administered rectally, for example, in the form of suppositories, or parenterally, for example, in the form of injection solutions.

Compounds have a high affinity and selectivity for GABA A α5 receptor binding sites. Therefore, the invention provides methods for enhancing cognition and methods for the treatment of cognitive disorders, such as Alzheimer's disease. In particular, the invention provides a method for the treatment of Alzheimer's disease which comprises administering a therapeutically effective amount of a compound of formula I or a pharmaceutically acceptable acid addition salt thereof.

The dosage at which compounds of the invention can be administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples 1-51 are provided for illustration of the invention. They should not be considered as limiting the scope of the invention, but merely as being representative thereof. Example 1 has been described in detail, the remaining compounds have been prepared accordingly.

EXAMPLE 1

3-[3-(4-Fluoro-phenyl)-5-methyl-isoxazole-4-carbonyl]-1H-indole-6-carboxylic acid cyclopropylmethyl-amide a) Step 1:

3-[3-(4-Fluoro-phenyl)-5-methyl-isoxazole-4-carbonyl]-1H-indole-6-carboxylic acid methyl ester To a stirred solution of 1.75 g (10 mmol) methyl indole-6-carboxylate (commercially available) in 15 mL of dry $CH_2Cl_2$ under argon at 0° C. was added 1.41 mL (12 mmol) of $SnCl_4$ in one portion. After removing the ice-bath, the mixture was stirred for 40 min at room temperature and then 2.39 g (10 mmol) of 3-(4-fluoro-phenyl)-5-methyl-isoxazole-4-carboxylic acid chloride (Prepared from the corresponding acid according to: J. Agric. Food Chem. 1995, 43, 219-228.) in 5 mL of $CH_2Cl_2$ was added at 0° C. followed by the addition of 15 mL of nitromethane in one portion. The mixture was stirred for 15 minutes at 0° C., after which 50 mL of ice-water was added to quench the reaction. The organic phase was separated and the aqueous solution was extracted with $CH_2Cl_2$ (2×20 mL). The combined extracts were washed with brine (30 mL), dried over $Na_2SO_4$, and evaporated to give 3.5 g of crude product (purity ~30%, LCMS) as brown semi-solid. The crude product was further washed with ethyl acetate to give 0.85 g of the title compound in 23% yield as a light-yellow powder. (m/e): 379.2 ($MH^+$; 100%).

b) Step 2:

3-[3-(4-Fluoro-phenyl)-5-methyl-isoxazole-4-carbonyl]-1H-indole-6-carboxylic acid (intermediate 1)

To a solution of 0.7 g (1.85 mmol) 3-[3-(4-fluoro-phenyl)-5-methyl-isoxazole-4-carbonyl]-1H-indole-6-carboxylic acid methyl ester in 12 mL of THF and 6 mL of $H_2O$, was added 0.39 g (9.25 mmol) $LiOH.H_2O$ in one portion. The reaction mixture was heated under reflux for 16 h. After the evaporation the mixture was extracted with Et$_2$O (10 mL), and acidified to pH=2-3 with 2 N HCl. The resulting solid was filtered off, washed with water and dried to give 0.65 g of the title compound (intermediate 1) in 97% yield as a white solid. (m/e): 365.1 (MH$^+$; 100%).

c) Step 3:

3-[3-(4-Fluoro-phenyl)-5-methyl-isoxazole-4-carbonyl]-1H-indole-6-carboxylic acid cyclopropylmethyl-amide A solution of 62 mg (0.17 mmol) 3-[3-(4-fluoro-phenyl)-5-methyl-isoxazole-4-carbonyl]-1H-indole-6-carboxylic acid, 41 mg (0.21 mmol) N-(3-dimethylaminopropyl)-N'-ethyl carbodiimide, 23 mg (0.17 mmol) 1-hydroxy benzotriazole, 59 uL (0.43 mmol) Et$_3$N and 0.26 mmol cyclopropylamine in DMF (1 mL) was reacted at room temperature overnight. After evaporation the mixture was subjected to preparative HPLC purification on reversed phase eluting with an acetonitrile/water (0.05% NEt$_3$) gradient to afford 51 mg of the title compound in 72% yield as a white solid. (m/e): 418.1 (MH$^+$; 100%).

Intermediate 2

3-(5-Methyl-3-phenyl-isoxazole-4-carbonyl)-1H-indole-6-carboxylic acid a) Step 1:

3-(5-Methyl-3-phenyl-isoxazole-4-carbonyl)-1H-indole-6-carboxylic acid methyl ester According to the procedure described for the synthesis of Example 1 (step 1) the title compound was obtained from methyl indole-6-carboxylate (commercially available) and 5-methyl-3-phenylisoxazole-4-carbonyl chloride (commercially available) in 20% yield as a light yellow solid. (m/e): 361.2 (MH$^+$; 100%).

b) Step 2:

3-(5-Methyl-3-phenyl-isoxazole-4-carbonyl)-1H-indole-6-carboxylic acid

According to the procedure described for the synthesis of Example 1 (step 2) the title compound (intermediate 2) was obtained from 3-(5-methyl-3-phenyl-isoxazole-4-carbonyl)-1H-indole-6-carboxylic acid methyl ester through saponification with LiOH.H$_2$O in 95% yield as a white solid. (m/e): 347.1 (MH$^+$; 100%).

Intermediate 3

3-[3-(3-Fluoro-phenyl)-5-methyl-isoxazole-4-carbonyl]-1H-indole-6-carboxylic acid a) Step 1:

3-[3-(3-Fluoro-phenyl)-5-methyl-isoxazole-4-carbonyl]-1H-indole-6-carboxylic acid methyl ester According to the procedure described for the synthesis of Example 1 (step 1) the title compound was prepared from 1H-indole-6-carboxylic acid methyl ester (commercially available) and 3-(3-fluoro-phenyl)-5-methyl-isoxazole-4-carboxylic acid (WO2001029015A2) which was obtained in 21% yield as a light yellow solid. (m/e): 379.1 (MH$^+$; 100%).

b) Step 2:

3-[3-(3-Fluoro-phenyl)-5-methyl-isoxazole-4-carbonyl]-1H-indole-6-carboxylic acid According to the procedure described for the synthesis of Example 1 (step 2) the title compound (intermediate 3) was prepared from 3-[3-(3-fluoro-phenyl)-5-methyl-isoxazole-4-carbonyl]-1H-indole-6-carboxylic acid methyl ester through saponification with LiOH.H$_2$O which was obtained in 88% yield as a light yellow solid. (m/e): 365.0 (MH$^+$; 100%).

Intermediate 4

3-[3-(3-Fluoro-phenyl)-5-isopropyl-isoxazole-4-carbonyl]-1H-indole-6-carboxylic acid a) Step 1:

5-Isopropyl-3-(3-fluoro-phenyl)-isoxazole-4-carboxylic acid ethyl ester

To a stirred solution of 3.39 g (53 mmol) of NaOEt in 30 mL of EtOH, at 0° C., was added dropwise 8.56 mL (53 mmol) of ethyl isobutyrylacetate (commercially available) in 10 mL of EtOH. The reaction mixture was stirred at room temperature for 40 minutes, and then 8.68 g (0.05 mol) solution of 3-fluoro-benzaldehyde-chloro-oxime (Prepared according to: J. Agric. Food Chem. 1995, 43, 219-228.) in 30 mL of EtOH was added dropwise in an ice-bath and the resulting suspension was stirred at room temperature for 2 h. The mixture was then evaporated and the residue partitioned between 200 mL of ethyl acetate and 100 mL of H$_2$O. The aqueous phase was then separated and extracted with ethyl acetate (2×60 mL). The combined organic extracts were washed with brine (100 mL), dried over Na$_2$SO$_4$ and evaporated to give 15 g of crude product (purity ~30%) as a yellow syrup. The crude product was used in the subsequent hydrolysis without purification.

5-Isopropyl-3-(3-fluoro-phenyl)-isoxazole-4-carboxylic acid

A mixture of 15 g crude 5-isopropyl-3-(3-fluoro-phenyl)-isoxazole-4-carboxylic acid ethyl ester and 10.08 g (240 mmol) LiOH.H$_2$O in 75 mL THF, 50 mL water was heated under reflux for 15 h. The mixture was concentrated, acidified and extracted with ethyl acetate. The combined organic extracts were dried with Na$_2$SO$_4$ and evaporated to yield 4.1 g (33% in two steps) of the title compound as a light yellow solid. (m/e): 250.1 (MH$^+$; 100%).

b) Step 2:

3-[3-(3-Fluoro-phenyl)-5-isopropyl-isoxazole-4-carbonyl]-1H-indole-6-carboxylic acid methyl ester According to the procedure described for the synthesis of Example 1 (step 1) the title compound was prepared from 1H-indole-6-carboxylic acid methyl ester (commercially available) and 3-(3-fluoro-phenyl)-5-isopropyl-isoxazole-4-carboxylic acid which was obtained in 17% yield as a yellow solid. (m/e): 407.1 (MH$^+$; 100%).

c) Step 3:

3-[3-(3-Fluoro-phenyl)-5-isopropyl-isoxazole-4-carbonyl]-1H-indole-6-carboxylic acid According to the procedure described for the synthesis of Example 1 (step 2) the title compound (intermediate 4) was prepared from 3-[3-(3-fluoro-phenyl)-5-isopropyl-isoxazole-4-carbonyl]-1H-indole-6-carboxylic acid methyl ester through saponification with LiOH.H$_2$O which was obtained in 75% yield as a light yellow solid. (m/e): 393.1 (MH$^+$; 100%).

Intermediate 5

3-[3-(3-Fluoro-phenyl)-5-methyl-isoxazole-4-carbonyl]-1-methyl-1H-indole-6-carboxylic acid a) Step 1:

3-[3-(3-Fluoro-phenyl)-5-methyl-isoxazole-4-carbonyl]-1-methyl-1H-indole-6-carboxylic acid methyl ester According to the procedure described for the synthesis of Example 1 (step 1) the title compound was prepared from N-methylindole-6-carboxylic acid methyl ester (commercially available) and 3-(3-fluoro-phenyl)-5-methyl-isoxazole-4-carboxylic acid (WO2001029015A2) which was obtained in 40% yield as a brown powder. (m/e): 393.0 (MH$^+$; 100%).

b) Step 2:

3-[3-(3-Fluoro-phenyl)-5-methyl-isoxazole-4-carbonyl]-1-methyl-1H-indole-6-carboxylic acid According to the procedure described for the synthesis of Example 1 (step 2) the title compound (intermediate 5) was prepared from 3-[3-(3-fluoro-phenyl)-5-methyl-isoxazole-4-carbonyl]-1-methyl-1H-indole-6-carboxylic acid methyl ester through saponification with LiOH.H$_2$O which was obtained in 92% yield as a red powder. (m/e): 379.1 (MH$^+$; 100%).

Intermediate 6

3-[3-(3-Fluoro-phenyl)-5-methyl-isoxazole-4-carbonyl]-1-phenyl-1H-indole-6-carboxylic acid a) Step 1:

3-[3-(3-Fluoro-phenyl)-5-methyl-isoxazole-4-carbonyl]-1-phenyl-1H-indole-6-carboxylic acid methyl ester According to the procedure described for the synthesis of Example 1 (step 1) the title compound was prepared from 1-phenyl-1H-indole-6-carboxylic acid methyl ester (WO2003004027A1) and 3-(3-fluoro-phenyl)-5-methyl-isoxazole-4-carboxylic acid (WO2001029015A2) which was obtained in 45% yield as a light yellow powder. (m/e): 455.1 (MH$^+$; 100%).

b) Step 2:

3-[3-(3-Fluoro-phenyl)-5-methyl-isoxazole-4-carbonyl]-1-phenyl-1H-indole-6-carboxylic acid According to the procedure described for the synthesis of Example 1 (step 2) the title compound (intermediate 6) was prepared from 3-[3-(3-fluoro-phenyl)-5-methyl-isoxazole-4-carbonyl]-1-phenyl-1H-indole-6-carboxylic acid methyl ester which was obtained in 93% yield as a light yellow solid. (m/e): 441.0 (MH$^+$; 100%).

According to the procedure described for the synthesis of Example 1 further aryl-isoxazole-4-carbonyl-indole-carboxylic acid amide derivatives have been synthesised from the respective intermediates mentioned in table 1 and the respective amines mentioned in table 1. The compounds are compiled in table 1 and comprise Example 2 to Example 51.

TABLE 1

| No. | Structure | MW | Systematic Name | Starting materials | Ki h[uM] | MW found |
|---|---|---|---|---|---|---|
| 2 | 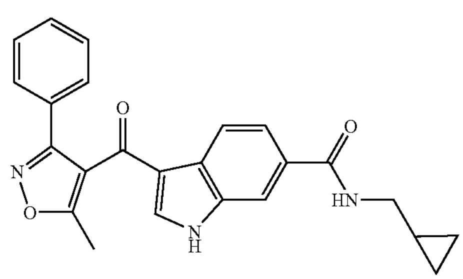 | 399.448 | 3-(5-Methyl-3-phenyl-isoxazole-4-carbonyl)-1H-indole-6-carboxylic acid cyclopropylmethyl-amide | 3-(5-Methyl-3-phenyl-isoxazole-4-carbonyl)-1H-indole-6-carboxylic acid (intermediate 1) and cyclopropylmethyl-amine (commercially available) | 0.00545 | 400.3 |

TABLE 1-continued

| No. | Structure | MW | Systematic Name | Starting materials | Ki h[uM] | MW found |
|---|---|---|---|---|---|---|
| 3 | 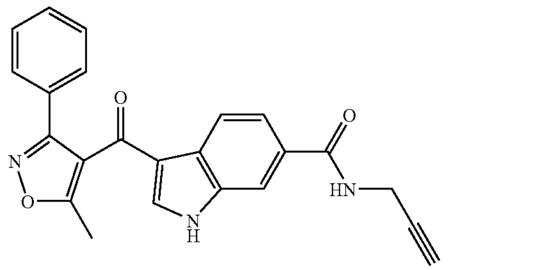 | 383.405 | 3-(5-Methyl-3-phenyl-isoxazole-4-carbonyl)-1H-indole-6-carboxylic acid prop-2-ynylamide | 3-(5-Methyl-3-phenyl-isoxazole-4-carbonyl)-1H-indole-6-carboxylic acid (intermediate 1) and prop-2-ynyl-amine (commercially available) | 0.0029 | 384.3 |
| 4 | 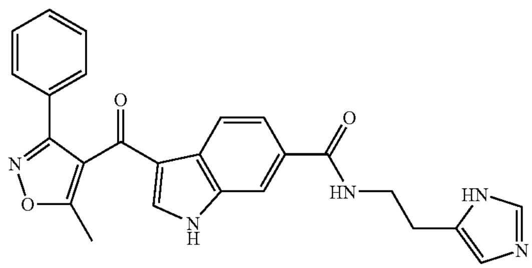 | 439.473 | 3-(5-Methyl-3-phenyl-isoxazole-4-carbonyl)-1H-indol-6-carboxylic acid [2-(1H-imidazol-4-yl)-ethyl]-amide | 3-(5-Methyl-3-phenyl-isoxazole-4-carbonyl)-1H-indole-6-carboxylic acid (intermediate 1) and 2-(1H-imidazol-4-yl)-ethyl-amine (commercially available) | 0.00265 | 440.3 |
| 5 | 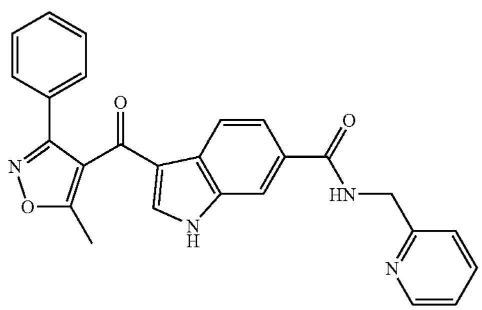 | 436.469 | 3-(5-Methyl-3-phenyl-isoxazole-4-carbonyl)-1H-indole-6-carboxylic acid (pyridin-2-ylmethyl)-amide | 3-(5-Methyl-3-phenyl-isoxazole-4-carbonyl)-1H-indole-6-carboxylic acid (intermediate 1) and pyridin-2-ylmethyl-amine (commercially available) | 0.00395 | 437.3 |
| 6 | 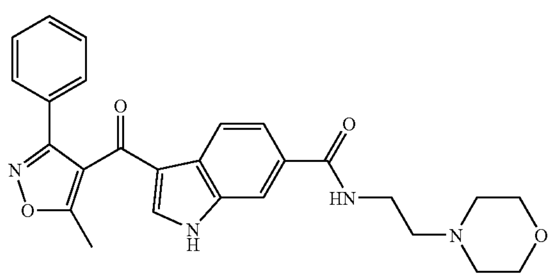 | 458.515 | 3-(5-Methyl-3-phenyl-isoxazole-4-carbonyl)-1H-indole-6-carboxylic acid (2-morpholin-4-yl-ethyl)-amide | 3-(5-Methyl-3-phenyl-isoxazole-4-carbonyl)-1H-indole-6-carboxylic acid (intermediate 1) and 2-morpholin-4-yl-ethyl-amine (commercially available) | 0.0033 | 459.3 |
| 7 | 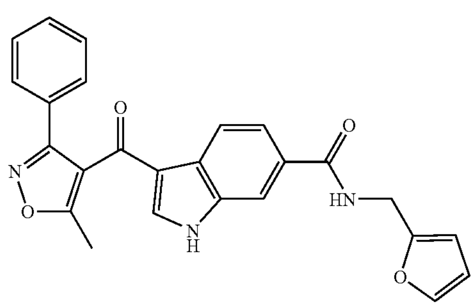 | 425.442 | 3-(5-Methyl-3-phenyl-isoxazole-4-carbonyl)-1H-indole-6-carboxylic acid (furan-2-ylmethyl)-amide | 3-(5-Methyl-3-phenyl-isoxazole-4-carbonyl)-1H-indole-6-carboxylic acid (intermediate 1) and furan-2-ylmethyl-amine (commercially available) | 0.0053 | 426.2 |

TABLE 1-continued

| No. | Structure | MW | Systematic Name | Starting materials | Ki h[uM] | MW found |
|---|---|---|---|---|---|---|
| 8 | 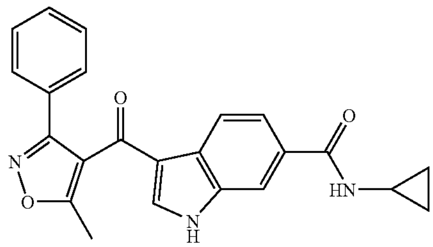 | 385.421 | 3-(5-Methyl-3-phenyl-isoxazole-4-carbonyl)-1H-indole-6-carboxylic acid cyclopropylamide | 3-(5-Methyl-3-phenyl-isoxazole-4-carbonyl)-1H-indole-6-carboxylic acid (intermediate 1) and cyclopropyl-amine (commercially available) | 0.003 | 386.2 |
| 9 | 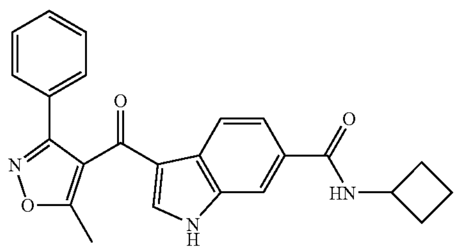 | 399.448 | 3-(5-Methyl-3-phenyl-isoxazole-4-carbonyl)-1H-indole-6-carboxylic acid cyclobutylamide | 3-(5-Methyl-3-phenyl-isoxazole-4-carbonyl)-1H-indole-6-carboxylic acid (intermediate 1) and cyclobutyl-amine (commercially available) | 0.00435 | 400.2 |
| 10 | 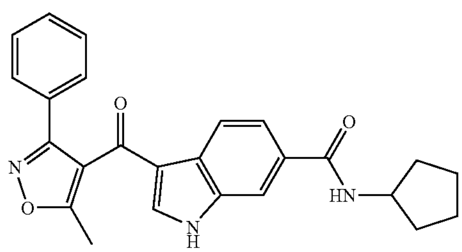 | 413.475 | 3-(5-Methyl-3-phenyl-isoxazole-4-carbonyl)-1H-indole-6-carboxylic acid cyclopentylamide | 3-(5-Methyl-3-phenyl-isoxazole-4-carbonyl)-1H-indole-6-carboxylic acid (intermediate 1) and cyclopentyl-amine (commercially available) | 0.0137 | 414.3 |
| 11 | 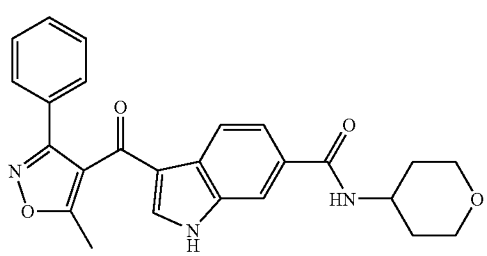 | 429.474 | 3-(5-Methyl-3-phenyl-isoxazole-4-carbonyl)-1H-indole-6-carboxylic acid (tetrahydro-pyran-4-yl)-amide | 3-(5-Methyl-3-phenyl-isoxazole-4-carbonyl)-1H-indole-6-carboxylic acid (intermediate 1) and tetrahydro-pyran-4-yl-amine (commercially available) | 0.00545 | 430.2 |
| 12 | 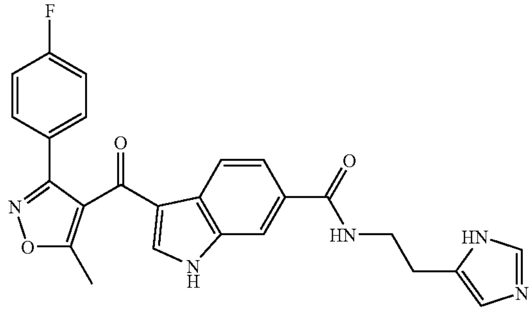 | 457.463 | 3-[3-(4-Fluoro-phenyl)-5-methyl-isoxazole-4-carbonyl]-1H-indole-6-carboxylic acid [2-(1H-imidazol-4-yl)-ethyl]-amide | 3-[3-(4-Fluoro-phenyl)-5-methyl-isoxazole-4-carbonyl)-1H-indole-6-carboxylic acid (intermediate 2) and 2-(1H-imidazol-4-yl)-ethyl-amide | 0.0026 | 458.0 |

TABLE 1-continued

| No. | Structure | MW | Systematic Name | Starting materials | Ki h[uM] | MW found |
|---|---|---|---|---|---|---|
| 13 | 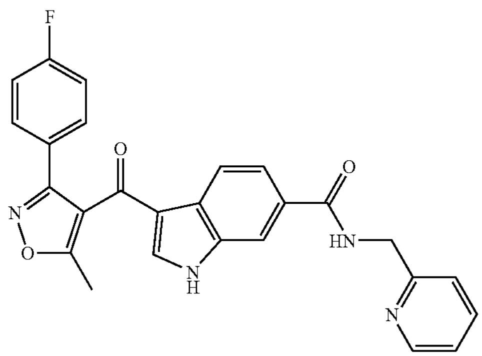 | 454.459 | 3-[3-(4-Fluoro-phenyl)-5-methyl-isoxazole-4-carbonyl]-1H-indole-6-carboxylic acid (pyridin-2-ylmethyl)-amide | 3-[3-(4-Fluoro-phenyl)-5-methyl-isoxazole-4-carbonyl]-1H-indole-6-carboxylic acid (intermediate 2) and pyridin-2-ylmethyl-amine (commercially available) | 0.00565 | 455.1 |
| 14 | 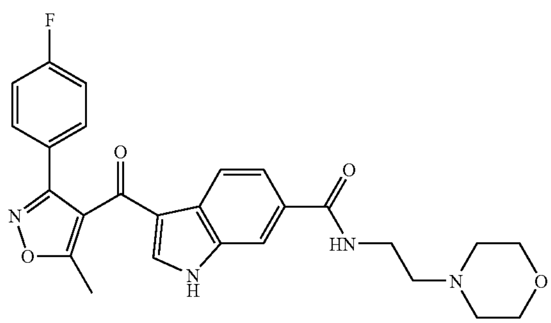 | 476.505 | 3-[3-(4-Fluoro-phenyl)-5-methyl-isoxazole-4-carbonyl]-1H-indole-6-carboxylic acid (2-morpholin-4-yl-ethyl)-amide | 3-[3-(4-Fluoro-phenyl)-5-meethyl-isoxazole-4-carbonyl]-1H-indole-6-carboxylic acid (intermediate 2) and 2-morpholin-4-yl-ethyl-amine (commercially available) | 0.00455 | 477.1 |
| 15 | 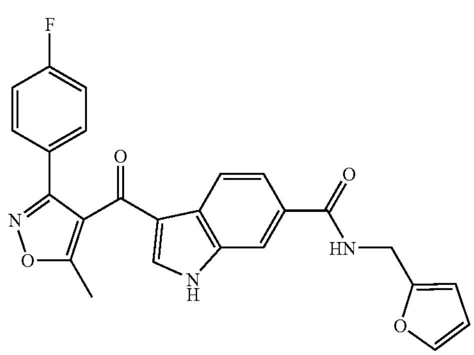 | 443.432 | 3-[3-(4-Fluoro-phenyl)-5-methyl-isoxazole-4-carbonyl]-1H-indole-6-carboxylic acid (furan-2-ylmethyl)-amide | 3-[3-(4-Fluoro-phenyl)-5-methyl-isoxazole-4-carbonyl]-1H-indole-6-carboxylic acid (intermediate 2) and furan-2-ylmethyl-amine (commercially available) | 0.00485 | 444.0 |
| 16 | 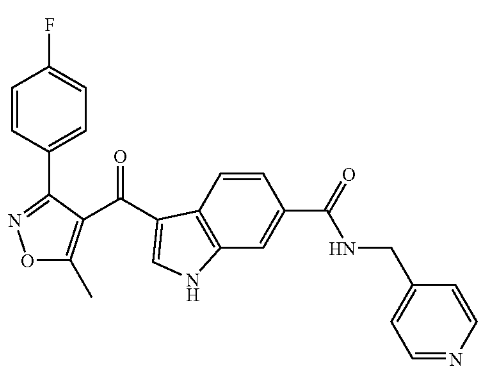 | 454.459 | 3-[3-(4-Fluoro-phenyl)-5-methyl-isoxazole-4-carbonyl]-1H-indole-6-carboxylic acid (pyridin-4-ylmethyl)-amide | 3-[3-(4-Fluoro-phenyl)-5-methyl-isoxazole-4-carbonyl]-1H-indole-6-carboxylic acid (intermediate 2) and pyridin-4-ylmethyl-amine | 0.00365 | 455.0 |

TABLE 1-continued

| No. | Structure | MW | Systematic Name | Starting materials | Ki h[uM] | MW found |
|---|---|---|---|---|---|---|
| 17 | 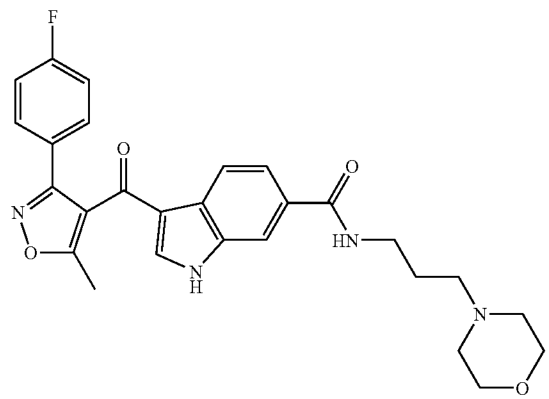 | 490.532 | 3-[3-(4-Fluoro-phenyl)-5-methyl-isoxazole-4-carbonyl]-1H-indole-6-carboxylic acid (3-morpholin-4-yl-propyl)-amide | 3-[3-(4-Fluoro-phenyl)-5-methyl-isoxazole-4-carbonyl]-1H-indole-6-carboxylic acid (intermediate 2) and 3-morpholin-4-yl-propyl-amine (commercially available) | 0.0043 | 491.1 |
| 18 | 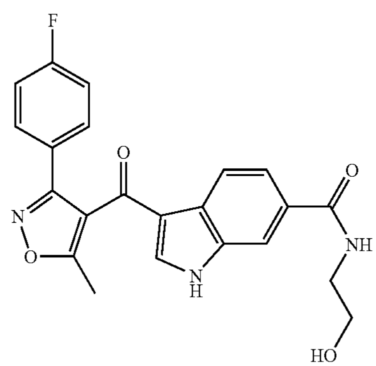 | 407.399 | 3-[3-(4-Fluoro-phenyl)-5-methyl-isoxazole-4-carbonyl]-1H-indole-6-carboxylic acid (2-hydroxy-ethyl)-amide | 3-[3-(4-Fluoro-phenyl)-5-methyl-isoxazole-4-carbonyl]-1H-indole-6-carboxylic acid (intermediate 2) and 2-hydroxy-ethyl-amine (commercially available) | 0.00185 | 408.0 |
| 19 | 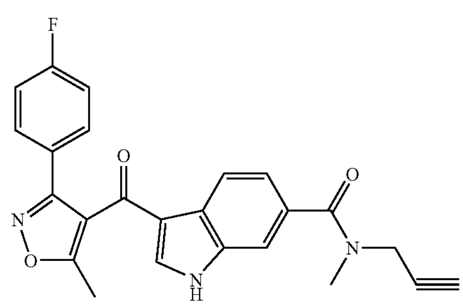 | 415.422 | 3-[3-(4-Fluoro-phenyl)-5-methyl-isoxazole-4-carbonyl]-1H-indole-6-carboxylic acid methyl-prop-2-ynyl-amide | 3-[3-(4-Fluoro-phenyl)-5-methyl-isoxazole-4-carbonyl]-1H-indole-6-carboxylic acid (intermediate 2) and methyl-prrop-2-ynyl-amine (commercially available) | 0.0606 | 416.0 |
| 20 | 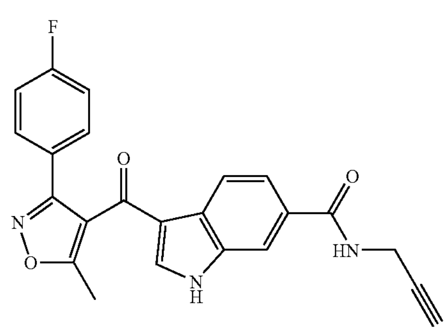 | 401.395 | 3-[3-(4-Fluoro-phenyl)-5-methyl-isoxazole-4-carbonyl]-1H-indole-6-carboxylic acid prop-2-ynylamide | 3-[3-(4-Fluoro-phenyl)-5-methyl-isoxazole-4-carbonyl]-1H-indole-6-carboxylic acid (intermediate 2) and prop-2-ynyl-amine (commercially available) | 0.00325 | 402.1 |

TABLE 1-continued

| No. | Structure | MW | Systematic Name | Starting materials | Ki h[uM] | MW found |
|---|---|---|---|---|---|---|
| 21 | 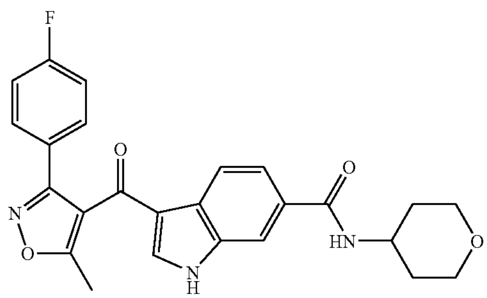 | 447.464 | 3-[3-(4-Fluoro-phenyl)-5-methyl-isoxazole-4-carbonyl]-1H-indole-6-carboxylic acid (tetrahydro-pyran-4-yl)-amide | 3-[3-(4-Fluoro-phenyl)-5-methyl-isoxazole-4-carbonyl]-1H-indole-6-carboxylic acid (intermediate 2) and tetrahydro-pyran-4-yl-amine (commercially available) | 0.005 | 448.0 |
| 22 | 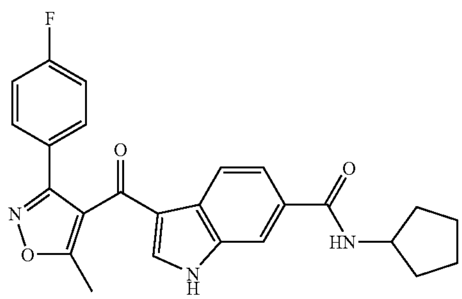 | 431.465 | 3-[3-(4-Fluoro-phenyl)-5-methyl-isoxazole-4-carbonyl]-1H-indole-6-carboxylic acid cyclopentylamide | 3-[3-(4-Fluoro-phenyl)-5-methyl-isoxazole-4-carbonyl]-1H-indole-6-carboxylic acid (intermediate 2) and cyclopentyl-amine (commercially available) | 0.00975 | 432.1 |
| 23 | 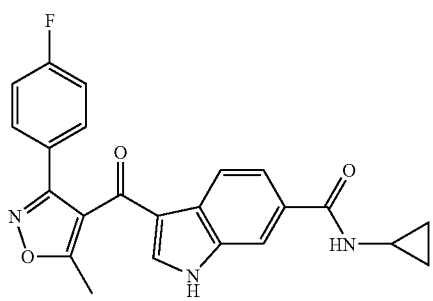 | 403.411 | 3-[3-(4-Fluoro-phenyl)-5-methyl-isoxazole-4-carbonyl]-1H-indole-6-carboxylic acid cyclopropylamide | 3-[3-(4-Fluoro-phenyl)-5-methyl-isoxazole-4-carbonyl]-1H-indole-6-carboxylic acid (intermediate 2) and cyclopropyl-amine (commercially available) | 0.00305 | 404.1 |
| 24 | 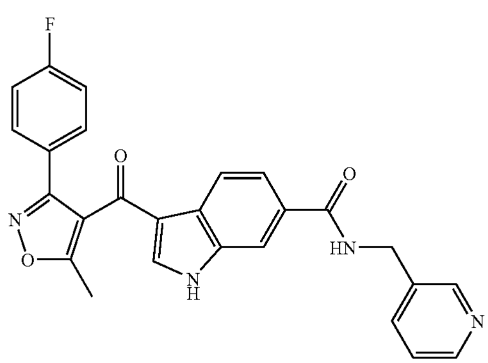 | 454.459 | 3-[3-(4-Fluoro-phenyl)-5-methyl-isoxazole-4-carbonyl]-1H-indole-6-carboxylic acid (pyridin-3-ylmethyl)-amide | 3-[3-(4-Fluoro-phenyl)-5-methyl-isoxazole-4-carbonyl]-1H-indole-6-carboxylic acid (intermediate 2) and pyridin-3-ylmethyl-amine (commercially available) | 0.00225 | 455.1 |
| 25 | 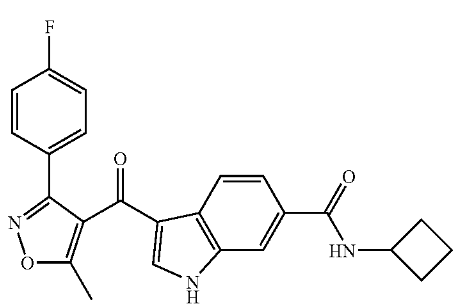 | 417.438 | 3-[3-(4-Fluoro-phenyl)-5-methyl-isoxazole-4-carbonyl]-1H-indole-6-carboxylic acid cyclobutylamide | 3-[3-(4-Fluoro-phenyl)-5-methyl-isoxazole-4-carbonyl]-1H-indole-6-carboxylic acid (intermediate 2) and cyclobutyl-amine (commercially available) | 0.00675 | 418.1 |

TABLE 1-continued

| No. | Structure | MW | Systematic Name | Starting materials | Ki h[uM] | MW found |
|---|---|---|---|---|---|---|
| 26 | 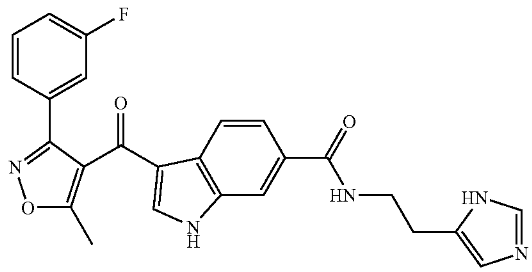 | 457.463 | 3-[3-(3-Fluoro-phenyl)-5-methyl-isoxazole-4-carbonyl]-1H-indole-6-carboxylic acid [2-(1H-imidazol-4-yl)-ethyl]-amide | 3-[3-(3-Fluoro-phenyl)-5-methyl-isoxazole-4-carbonyl]-1-methyl-1H-indole-6-carboxylic acid (intermediate 3) and 2-(1H-imidazol-4-yl)-ethyl-amine (commercially available) | 0.02355 | 458.2 |
| 27 | 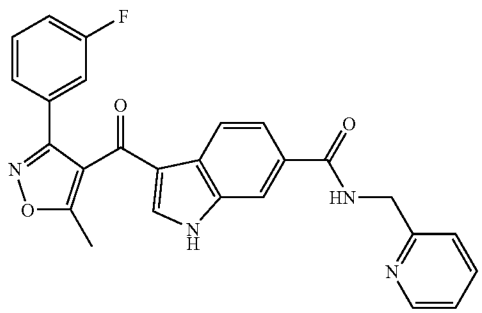 | 454.459 | 3-[3-(3-Fluoro-phenyl)-5-methyl-isoxazole-4-carbonyl]-1H-indole-6-carboxylic acid (pyridin-2-ylmethyl)-amide | 3-[3-(3-Fluoro-phenyl)-5-methyl-isoxazole-4-carbonyl]-1-methyl-1H-indole-6-carboxylic acid (intermediate 3) and pyridin-2-ylmethyl-amine (commercially available) | 0.0394 | 455.1 |
| 28 | 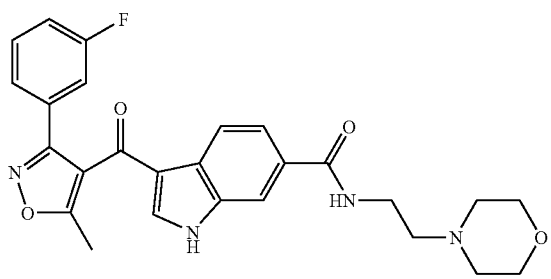 | 476.505 | 3-[3-(3-Fluoro-phenyl)-5-methyl-isoxazole-4-carbonyl]-1H-indole-6-carboxylic acid (2-morpholin-4-yl-ethyl)-amide | 3-[3-(3-Fluoro-phenyl)-5-methyl-isoxazole-4-carbonyl]-1-methyl-1H-indole-6-carboxylic acid (intermediate 3) and 2-morpholin-4-yl-ethyl-amine (commercially available) | 0.02275 | 477.2 |
| 29 | 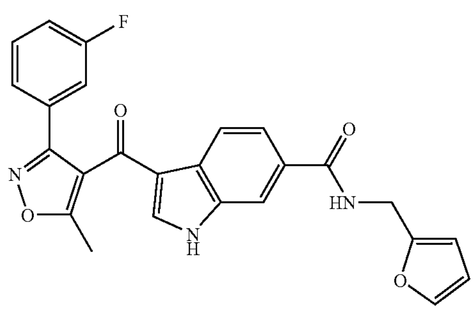 | 443.432 | 3-[3-(3-Fluoro-phenyl)-5-methyl-isoxazole-4-carbonyl]-1H-indole-6-carboxylic acid (furan-2-ylmethyl)-amide | 3-[3-(3-Fluoro-phenyl)-5-methyl-isoxazole-4-carbonyl]-1-methyl-1H-indole-6-carboxylic acid (intermediate 3) and furan-2-ylmethyl-amine (commercially available) | 0.0621 | 444.1 |
| 30 | 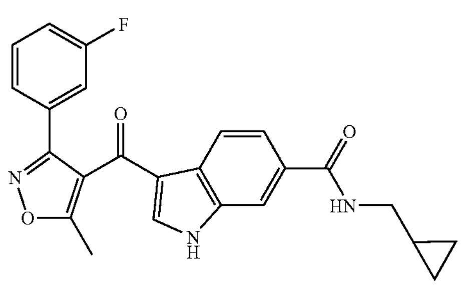 | 417.438 | 3-[3-(3-Fluoro-phenyl)-5-methyl-isoxazole-4-carbonyl]-1H-indole-6-carboxylic acid cyclopropylmethyl-amide | 3-[3-(3-Fluoro-phenyl)-5-methyl-isoxazole-4-carbonyl]-1-methyl-1H-indole-6-carboxylic acid (intermediate 3) and cyclopropylmethyl-amine (commercially available) | 0.0537 | 418.1 |

TABLE 1-continued

| No. | Structure | MW | Systematic Name | Starting materials | Ki h[uM] | MW found |
|---|---|---|---|---|---|---|
| 31 | 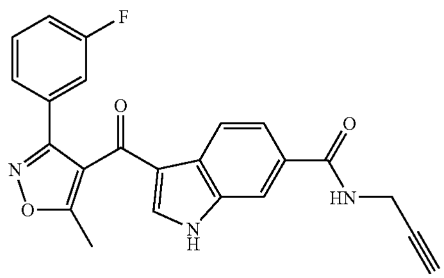 | 401.395 | 3-[3-(3-Fluoro-phenyl)-5-methyl-isoxazole-4-carbonyl]-1H-indole-6-carboxylic acid prop-2-ynylamide | 3-[3-(3-Fluoro-phenyl)-5-methyl-isoxazole-4-carbonyl]-1-methyl-1H-indole-6-carboxylic acid (intermediate 3) and prop-22-ynyl-amine (commercially available) | 0.0319 | 402.1 |
| 32 | 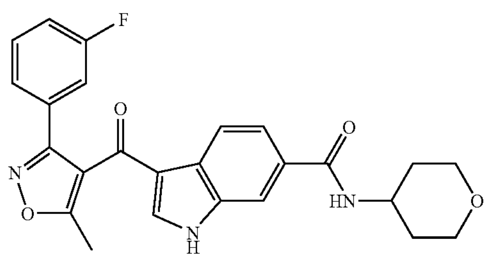 | 447.464 | 3-[3-(3-Fluoro-phenyl)-5-methyl-isoxazole-4-carbonyl]-1H-indole-6-carboxylic acid (tetrahydro-pyran-4-yl)-amide | 3-[3-(3-Fluoro-phenyl)-5-methyl-isoxazole-4-carbonyl]-1-methyl-1H-indole-6-carboxylic acid (intermediate 3) and tetrahydro-pyran-4-yl-amine (commercially available) | 0.0418 | 448.1 |
| 33 | 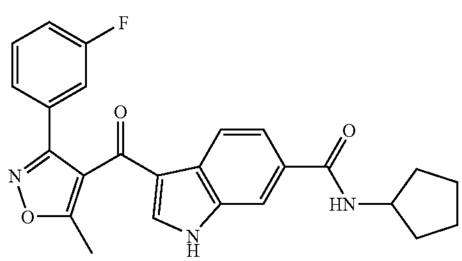 | 431.465 | 3-[3-(3-Fluoro-phenyl)-5-methyl-isoxazole-4-carbonyl]-1H-indole-6-carboxylic acid cyclopentylamide | 3-[3-(3-Fluoro-phenyl)-5-methyl-isoxazole-4-carbonyl]-1-methyl-1H-indole-6-carboxylic acid (intermediate 3) and cyclopentyl-amine (commercially available) | 0.0953 | 432.1 |
| 34 | 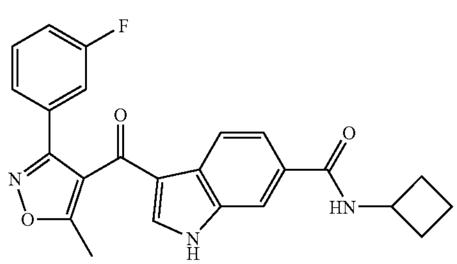 | 417.438 | 3-[3-(3-Fluoro-phenyl)-5-methyl-isoxazole-4-carbonyl]-1H-indole-6-carboxylic acid cyclobutylamide | 3-[3-(3-Fluoro-phenyl)-5-methyl-isoxazole-4-carbonyl]-1-methyl-1H-indole-6-carboxylic acid (intermediate 3) and cyclobutyl-amine (commercially available) | 0.05895 | 418.1 |
| 35 | 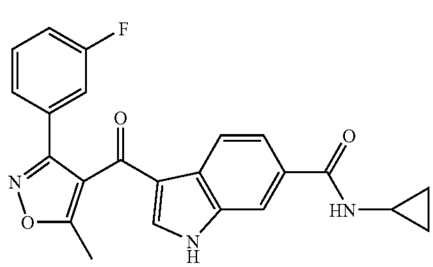 | 403.411 | 3-[3-(3-Fluoro-phenyl)-5-methyl-isoxazole-4-carbonyl]-1H-indole-6-carboxylic acid cyclopropylamide | 3-[3-(3-Fluoro-phenyl)-5-methyl-isoxazole-4-carbonyl]-1-methyl-1H-indole-6-carboxylic acid (intermediate 3) and cyclopropyl-amine (commercially available) | 0.03805 | 404.1 |

TABLE 1-continued

| No. | Structure | MW | Systematic Name | Starting materials | Ki h[uM] | MW found |
|---|---|---|---|---|---|---|
| 36 | 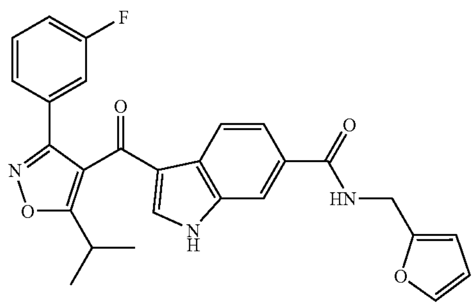 | 471.486 | 3-[3-(3-Fluoro-phenyl)-5-isopropyl-isoxazole-4-carbonyl]-1H-indole-6-carboxylic acid (furan-2-ylmethyl)-amide | 3-[3-(3-Fluoro-phenyl)-5-isopropyl-isoxazole-4-carbonyl]-1H-indole-6-carboxylic acid (intermediate 4) and furan-2-ylmethyl-amine (commercially available) | 0.04535 | 472.0 |
| 37 | 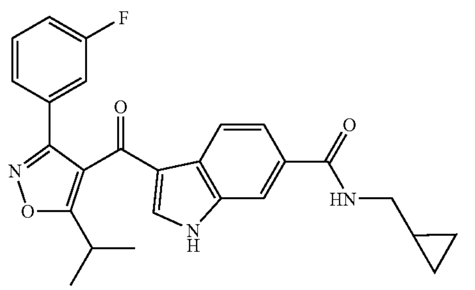 | 445.492 | 3-[3-(3-Fluoro-phenyl)-5-isopropyl-isoxazole-4-carbonyl]-1H-indole-6-carboxylic acid cyclopropylmethyl-amide | 3-[3-(3-Fluoro-phenyl-5-isopropyl-isoxazole-4-carbonyl]-1H-indole-6-carboxylic acid (intermediate 4) and cyclopropylmethyl-amine (commercially available) | 0.03935 | 446.1 |
| 38 | 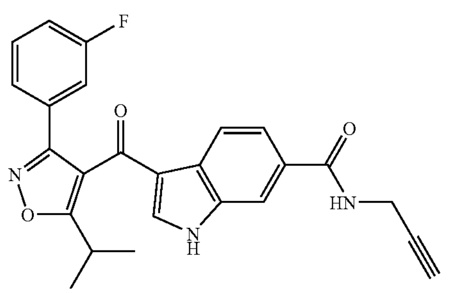 | 429.449 | 3-[3-(3-Fluoro-phenyl)-5-isopropyl-isoxazole-4-carbonyl]-1H-indole-6-carboxylic acid prop-2-ynylamide | 3-[3-(3-Fluoro-pheenyl)-5-isopropyl-isoxazole-4-carbonyl]-1H-indole-6-carboxylic acid (intermediate 4) and prop-2-ynyl-amine (commercially available) | 0.03155 | 430.0 |
| 39 | 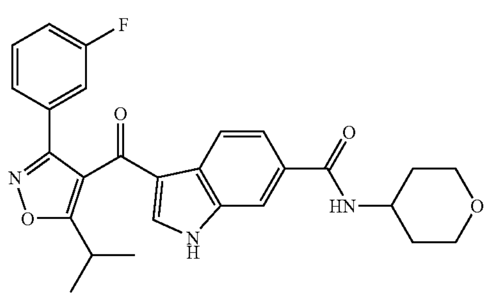 | 475.517 | 3-[3-(3-Fluoro-phenyl)-5-isopropyl-isoxazole-4-carbonyl]-1H-indole-6-carboxylic acid (tetrahydro-pyran-4-yl)-amide | 3-[3-(3-Fluoro-phenyl)-5-isopropyl-isoxazole-4-carbonyl]-1H-indole-6-carboxylic acid (intermediate 4) and tetrahydro-pyran-4-yl-amine (commercially available) | 0.03865 | 476.1 |
| 40 | 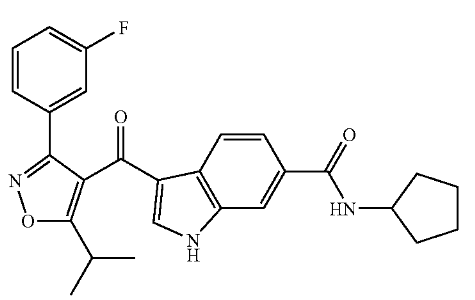 | 459.518 | 3-[3-(3-Fluoro-phenyl)-5-isopropyl-isoxazole-4-carbonyl]-1H-indole-6-carboxylic acid cyclopentylamide | 3-[3-(3-Fluoro-phenyl)-5-isopropyl-isoxazole-4-carbonyl]-1H-indole-6-carboxylic acid (intermediate 4) and cyclopentyl-amine (commercially available) | 0.0447 | 460.1 |

TABLE 1-continued

| No. | Structure | MW | Systematic Name | Starting materials | Ki h[uM] | MW found |
|---|---|---|---|---|---|---|
| 41 | 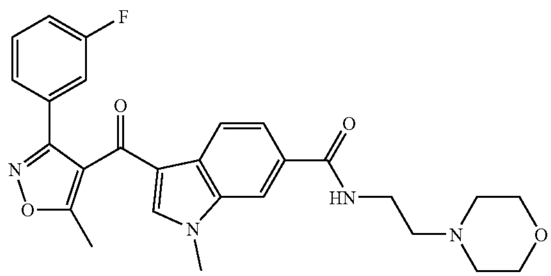 | 490.532 | 3-[3-(3-Fluoro-phenyl)-5-methyl-isoxazole-4-carbonyl]-1-methyl-1H-indole-6-carboxylic acid (2-morpholin-4-yl-ethyl)-amide | 3-[3-(3-Fluoro-phenyl)-5-methyl-isoxazole-4-carbonyl]-1-methyl-1H-indole-6-carboxylic acid (intermediate 5) and 2-morpholin-4-yl-ethyl-amine (commercially available) | 0.0249 | 491.1 |
| 42 | 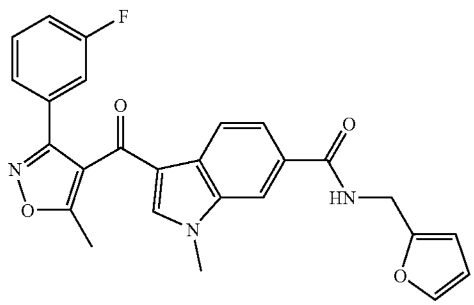 | 457.459 | 3-[3-(3-Fluoro-phenyl)-5-methyl-isoxazole-4-carbonyl]-1-methyl-1H-indole-6-carboxylic acid (furan-2-ylmethyl)-amide | 3-[3-(3-Fluoro-phenyl)-5-methyl-isoxazole-4-carbonyl]-1-methyl-1H-indole-6-carboxylic acid (intermediate 5) and furan-2-ylmethyl-amine (commercially available) | 0.07685 | 458.1 |
| 43 | 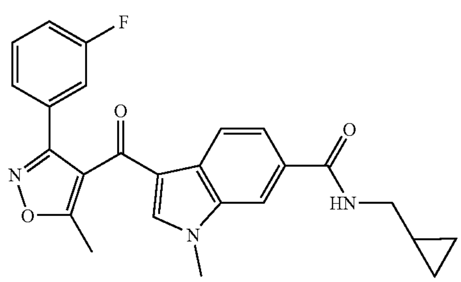 | 431.465 | 3-[3-(3-Fluoro-phenyl)-5-methyl-isoxazole-4-carbonyl]-1-methyl-1H-indole-6-carboxylic acid cyclopropylmethyl-amide | 3-[3-(3-Fluoro-phenyl)-5-methyl-isoxazole-4-carbonyl]-1-methyl-1H-indole-6-carboxylic acid (intermediate 5) and cyclopropylmethyl-amine (commercially available) | 0.06665 | 432.1 |
| 44 | 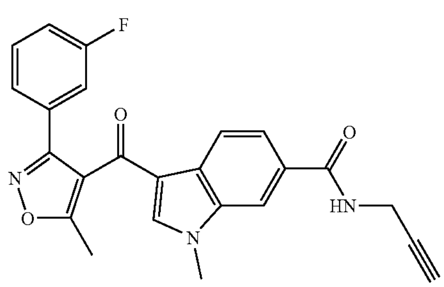 | 415.422 | 3-[3-(3-Fluoro-phenyl)-5-methyl-isoxazole-4-carbonyl]-1-methyl-1H-indole-6-carboxylic acid prop-2-ynylamide | 3-[3-(3-Fluoro-phenyl)-5-methyl-isoxazole-4-carbonyl]-1-methyl-1H-indole-6-carboxylic acid (intermediate 5) and prop-2-ynyl-amine (commercially available) | 0.0383 | 416.1 |
| 45 | 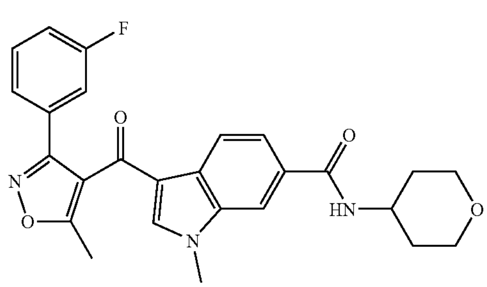 | 461.491 | 3-[3-(3-Fluoro-phenyl)-5-methyl-isoxazole-4-carbonyl]-1-methyl-1H-indole-6-carboxylic acid (tetrahydro-pyrann-4-yl)-amide | 3-[3-(3-Fluoro-phenyl)-5-methyl-isoxazole-4-carbonyl]-1-methyl-1H-indole-6-carboxylic acid (intermediate 5) and tetrahydro-pyran-4-yl-amine (commercially available) | 0.04905 | 462.2 |

TABLE 1-continued

| No. | Structure | MW | Systematic Name | Starting materials | Ki h[uM] | MW found |
|---|---|---|---|---|---|---|
| 46 | 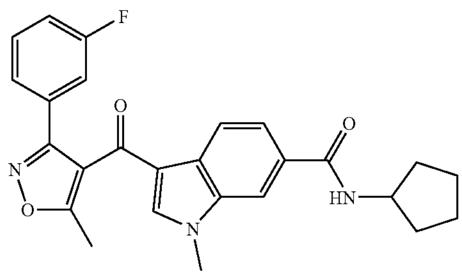 | 445.492 | 3-[3-(3-Fluorophenyl)-5-methyl-isoxazole-4-carbonyl]-1-methyl-1H-indole-6-carboxylic acid cyclopentylamide | 3-[3-(3-Fluorophenyl)-5-methyl-isoxazole-4-carbonyl]-1-methyl-1H-indole-6-carboxylic acid (intermediate 5) and cyclopentyl-amine (commercially available) | 0.1109 | 446.2 |
| 47 | 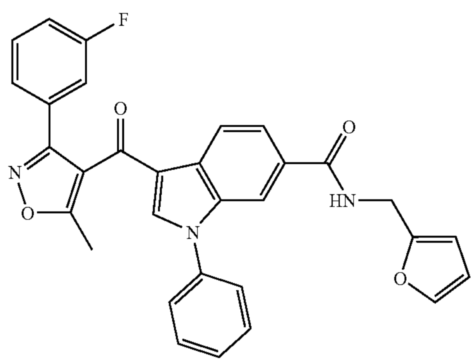 | 519.53 | 3-[3-(3-Fluorophenyl)-5-methyl-isoxazole-4-carbonyl]-1-phenyl-1H-indole-6-carboxylic acid (furan-2-ylmethyl)-amide | 3-[3-(3-Fluorophenyl)-5-methyl-isoxazole-4-carbonyl]-1-phenyl-1H-indole-6-carboxylic acid (intermediate 6) and furan-2-ylmethyl-amine (commercially available | 0.0253 | 520.1 |
| 48 | 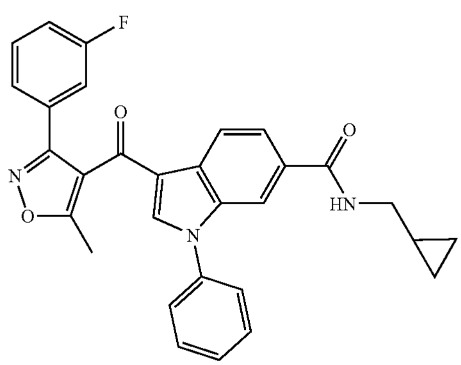 | 493.536 | 3-[3-(3-Fluorophenyl)-5-methyl-isoxazole-4-carbonyl]-1-phenyl-1H-indole-6-carboxylic acid cyclopropylmethyl-amide | 3-[3-(3-Fluorophenyl)-5-methyl-isoxazole-4-carbonyl]-1-phenyl-1H-indole-6-carboxylic acid (intermediate 6) and cyclopropylmethyl-amine (commercially available) | 0.0138 | 494.0 |
| 49 | 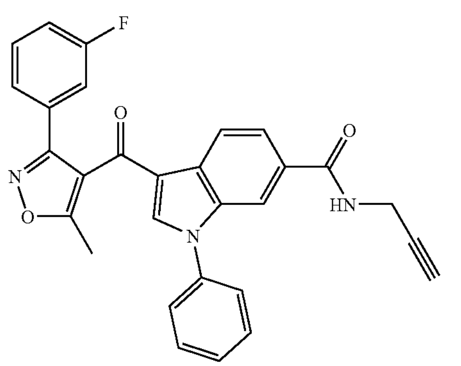 | 477.493 | 3-[3-(3-Fluorophenyl)-5-methyl-isoxazole-4-carbonyl]-1-phenyl-1H-indole-6-carboxylic acid prop-2-ynylamide | 3-[3-(3-Fluorophenyl)-5-methyl-isoxazole-4-carbonyl]-1-phenyl-1H-indole-6-carboxylic acid (intermediate 6) and prop-2-ynyl-amine (commercially available) | 0.0085 | 478.0 |

TABLE 1-continued

| No. | Structure | MW | Systematic Name | Starting materials | Ki h[uM] | MW found |
|---|---|---|---|---|---|---|
| 50 | 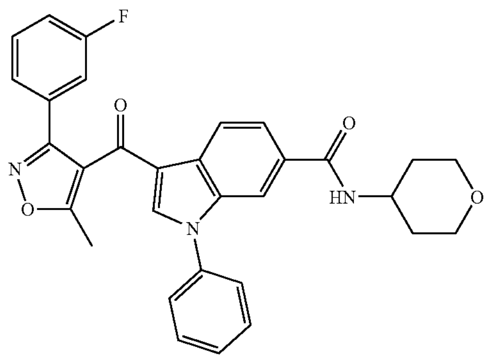 | 523.561 | 3-[3-(3-Fluoro-phenyl)-5-methyl-isoxazole-4-carbonyl]-1-phenyl-1H-indole-6-carboxylic acid (tetrahydro-pyran-4-yl)-amide | 3-[3-(3-Fluoro-phenyl)-5-methyl-isoxazole-4-carbonyl]-1-phenyl-1H-indole-6-carboxylic acid (intermediate 6) and tetrahydro-pyran-4-yl-amine (commercially available) | 0.0098 | 524.1 |
| 51 | 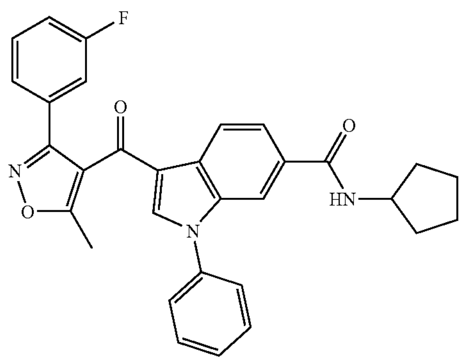 | 507.562 | 3-[3-(3-Fluoro-phenyl)-5-methyl-isoxazole-4-carbonyl]-1-phenyl-1H-indole-6-carboxylic acid cyclopentylamide | 3-[3-(3-Fluoro-phenyl)-5-methyl-isoxazole-4-carbonyl]-1-phenyl-1H-indole-6-carboxylic acid (intermediate 6) and cyclopentyl-amine (commercially available) | 0.04025 | 508.0 |

The invention claimed is:

1. An aryl-isoxazole-4-carbonyl-indole-carboxylic acid amide derivative of formula I

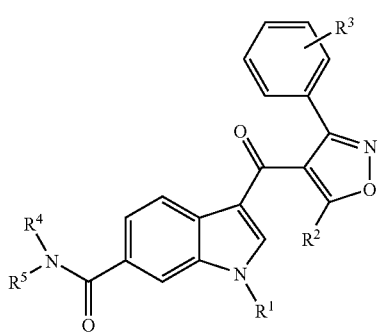

wherein
R$^1$ is hydrogen, lower alkyl or aryl;
R$^2$ is lower alkyl;
R$^3$ is hydrogen or halogen;
R$^4$ and R$^5$ are each independently hydrogen, lower alkyl, lower alkinyl, —(CH$_2$)$_n$-cycloalkyl, —(CH$_2$)$_n$-heteroaryl, —(CH$_2$)$_n$-heterocyclyl or —(CH$_2$)$_n$—OH; and
n is 0, 1, 2 or 3;
or a pharmaceutically acceptable acid addition salt thereof.

2. The compound of claim 1, wherein R$^4$ is hydrogen.

3. The compound of claim 2, wherein R$^5$ is lower alkinyl.

4. The compound of claim 3, selected from the group consisting of
  3-(5-methyl-3-phenyl-isoxazole-4-carbonyl)-1H-indole-6-carboxylic acid prop-2-ynylamide,
  3-[3-(4-fluoro-phenyl)-5-methyl-isoxazole-4-carbonyl]-1H-indole-6-carboxylic acid prop-2-ynylamide and
  3-[3-(3-fluoro-phenyl)-5-methyl-isoxazole-4-carbonyl]-1-phenyl-1H-indole-6-carboxylic acid prop-2-ynylamide.

5. The compound of claim 2, wherein R$^5$ is (CH$_2$)$_n$-cycloalkyl.

6. The compound of claim 5, selected from the group consisting of
  3-[3-(4-fluoro-phenyl)-5-methyl-isoxazole-4-carbonyl]-1H-indole-6-carboxylic acid cyclopropylmethyl-amide,
  3-(5-methyl-3-phenyl-isoxazole-4-carbonyl)-1H-indole-6-carboxylic acid cyclopropylmethyl-amide,
  3-(5-methyl-3-phenyl-isoxazole-4-carbonyl)-1H-indole-6-carboxylic acid cyclopropylamide,
  3-(5-methyl-3-phenyl-isoxazole-4-carbonyl)-1H-indole-6-carboxylic acid cyclobutylamide,
  3-[3-(4-fluoro-phenyl)-5-methyl-isoxazole-4-carbonyl]-1H-indole-6-carboxylic acid cyclopentylamide,
  3-[3-(4-fluoro-phenyl)-5-methyl-isoxazole-4-carbonyl]-1H-indole-6-carboxylic acid cyclopropylamide and
  3-[3-(4-fluoro-phenyl)-5-methyl-isoxazole-4-carbonyl]-1H-indole-6-carboxylic acid cyclobutylamide.

7. The compound of claim 2, wherein R$^5$ is (CH$_2$)$_n$-heteroaryl.

8. The compound of claim 7, selected from the group consisting of
- 3-(5-methyl-3-phenyl-isoxazole-4-carbonyl)-1H-indole-6-carboxylic acid [2-(1H-imidazol-4-yl)-ethyl]-amide,
- 3-(5-methyl-3-phenyl-isoxazole-4-carbonyl)-1H-indole-6-carboxylic acid (pyridin-2-ylmethyl)-amide,
- 3-(5-methyl-3-phenyl-isoxazole-4-carbonyl)-1H-indole-6-carboxylic acid (furan-2-ylmethyl)-amide,
- 3-[3-(4-fluoro-phenyl)-5-methyl-isoxazole-4-carbonyl]-1H-indole-6-carboxylic acid [2-(1H-imidazol-4-yl)-ethyl]-amide,
- 3-[3-(4-fluoro-phenyl)-5-methyl-isoxazole-4-carbonyl]-1H-indole-6-carboxylic acid (pyridin-2-ylmethyl)-amide,
- 3-[3-(4-fluoro-phenyl)-5-methyl-isoxazole-4-carbonyl]-1H-indole-6-carboxylic acid (furan-2-ylmethyl)-amide,
- 3-[3-(4-fluoro-phenyl)-5-methyl-isoxazole-4-carbonyl]-1H-indole-6-carboxylic acid (pyridin-4-ylmethyl)-amide and
- 3-[3-(4-fluoro-phenyl)-5-methyl-isoxazole-4-carbonyl]-1H-indole-6-carboxylic acid (pyridin-3-ylmethyl)-amide.

9. The compound of claim 2, wherein $R^5$ is $(CH_2)_n$-heterocyclyl.

10. The compound of claim 9, selected from the group consisting of
- 3-(5-methyl-3-phenyl-isoxazole-4-carbonyl)-1H-indole-6-carboxylic acid (2-morpholin-4-yl-ethyl)-amide,
- 3-(5-methyl-3-phenyl-isoxazole-4-carbonyl)-1H-indole-6-carboxylic acid (tetrahydro-pyran-4-yl)-amide,
- 3-[3-(4-fluoro-phenyl)-5-methyl-isoxazole-4-carbonyl]-1H-indole-6-carboxylic acid (2-morpholin-4-yl-ethyl)-amide,
- 3-[3-(4-fluoro-phenyl)-5-methyl-isoxazole-4-carbonyl]-1H-indole-6-carboxylic acid (3-morpholin-4-yl-propyl)-amide,
- 3-[3-(4-fluoro-phenyl)-5-methyl-isoxazole-4-carbonyl]-1H-indole-6-carboxylic acid (tetrahydro-pyran-4-yl)-amide and
- 3-[3-(3-fluoro-phenyl)-5-methyl-isoxazole-4-carbonyl]-1-phenyl-1H-indole-6-carboxylic acid (tetrahydro-pyran-4-yl)-amide.

11. The compound of claim 2, wherein $R^5$ is $(CH_2)_n$—OH.

12. The compound of claim 11, which compound is 3-[3-(4-fluoro-phenyl)-5-methyl-isoxazole-4-carbonyl]-1H-indole-6-carboxylic acid (2-hydroxy-ethyl)-amide.

13. The compound of claim 1, wherein $R^4$ is methyl.
14. The compound of claim 1, wherein $R^5$ is lower alkyl.
15. The compound of claim 1 wherein $R^5$ is lower alkinyl.
16. The compound of claim 15, wherein $R^1$ is hydrogen.
17. The compound of claim 15, wherein $R^1$ is lower alkyl.
18. The compound of claim 15, wherein $R^1$ is aryl.
19. The compound of claim 1, wherein $R^5$ is $(CH_2)_n$-cycloalkyl.
20. The compound of claim 19, wherein $R^1$ is hydrogen.
21. The compound of claim 19, wherein $R^1$ is lower alkyl.
22. The compound of claim 19, wherein $R^1$ is aryl.
23. The compound of claim 1, wherein R5 is (CH2)n-heteroaryl.
24. The compound of claim 23, wherein $R^1$ is hydrogen.
25. The compound of claim 23, wherein $R^1$ is lower alkyl.
26. The compound of claim 23, wherein $R^1$ is aryl.
27. The compound of claim 1, wherein $R^5$ is $(CH_2)_n$-heterocyclyl.
28. The compound of claim 27, wherein $R^1$ is hydrogen.
29. The compound of claim 27, wherein $R^1$ is lower alkyl.
30. The compound of claim 27, wherein $R^1$ is aryl.
31. The compound of claim 1, wherein $R^5$ is $(CH_2)_n$—OH.
32. The compound of claim 31, wherein $R^1$ is hydrogen.
33. A pharmaceutical composition comprising a therapeutically effective amount of a compound of formula I

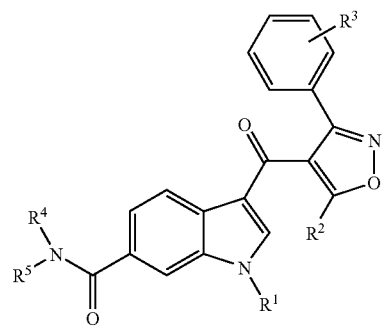

wherein
- $R^1$ is hydrogen, lower alkyl or aryl;
- $R^2$ is lower alkyl;
- $R^3$ is hydrogen or halogen;
- $R^4$ and $R^5$ are each independently hydrogen, lower alkyl, lower alkinyl, —$(CH_2)_n$-cycloalkyl, —$(CH_2)_n$-heteroaryl, —$(CH_2)_n$-heterocyclyl or —$(CH_2)_n$—OH; and
- n is 0, 1, 2 or 3;
- or a pharmaceutically acceptable acid addition salt thereof and a pharmaceutically acceptable carrier.

* * * * *